US009854981B2

(12) United States Patent
Hiltner

(10) Patent No.: US 9,854,981 B2
(45) Date of Patent: Jan. 2, 2018

(54) DEVICE AND METHODS FOR MEASURING AND TREATING AN ANATOMICAL STRUCTURE

(71) Applicant: ACIST Medical Systems, Inc., Eden Prairie, MN (US)

(72) Inventor: Jason Fredrick Hiltner, Minnetonka, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 1084 days.

(21) Appl. No.: 13/649,520

(22) Filed: Oct. 11, 2012

(65) Prior Publication Data
US 2013/0096409 A1    Apr. 18, 2013

Related U.S. Application Data

(60) Provisional application No. 61/547,306, filed on Oct. 14, 2011.

(51) Int. Cl.
*A61B 5/04*     (2006.01)
*A61B 18/18*    (2006.01)
(Continued)

(52) U.S. Cl.
CPC ............ *A61B 5/02055* (2013.01); *A61B 5/01* (2013.01); *A61B 5/0205* (2013.01);
(Continued)

(58) Field of Classification Search
CPC ...... A61B 18/1492; A61B 2018/00839; A61B 5/0422; A61B 2018/00351;
(Continued)

(56) References Cited

U.S. PATENT DOCUMENTS 4,587,975 A * 5/1986 Salo ..................... A61B 5/0535
600/506
4,928,693 A * 5/1990 Goodin ................. A61B 5/0215
600/434
(Continued)

FOREIGN PATENT DOCUMENTS

CN      101854853 A     10/2010
EP      1025805         8/2000
(Continued)

OTHER PUBLICATIONS

"PCT International Search Report and Written Opinion dated Jan. 21, 2013 for related application PCT/US2012/059718," 10 pgs.
(Continued)

*Primary Examiner* — Joseph Stoklosa
*Assistant Examiner* — Brian M Antiskay
(74) *Attorney, Agent, or Firm* — Fredrikson & Byron, P.A.

(57) ABSTRACT

A sensor delivery device and methods of using the device are provided, wherein the sensor delivery device includes a sensor that is adapted to obtain a measurement that can be used to calculate cross-sectional area of a surrounding anatomical structure. In certain cases, the sensor is an electrode arrangement, wherein the electrode arrangement generates a current and measures voltage resulting from the current. The voltage measurement is then used to calculate conductivity of fluid in the surrounding anatomical structure and thus cross-sectional area.

26 Claims, 12 Drawing Sheets

(51) Int. Cl.
- *A61B 5/0205* (2006.01)
- *A61B 5/01* (2006.01)
- *A61B 5/053* (2006.01)
- *A61B 5/107* (2006.01)
- *A61B 5/00* (2006.01)
- *A61F 2/82* (2013.01)
- *A61B 5/02* (2006.01)
- *A61B 5/0215* (2006.01)

(52) U.S. Cl.
CPC ...... *A61B 5/02007* (2013.01); *A61B 5/02154* (2013.01); *A61B 5/0535* (2013.01); *A61B 5/0538* (2013.01); *A61B 5/1076* (2013.01); *A61B 5/6851* (2013.01); *A61F 2/82* (2013.01)

(58) Field of Classification Search
CPC .... A61B 2017/003; A61B 2017/00053; A61B 2018/00357; A61B 2018/00797; A61B 2018/00821; A61B 2018/1435; A61B 2018/1467; A61B 5/6852; A61B 5/6857; A61B 2017/00084; A61B 2018/0016; A61B 2018/00642; A61M 25/01; A61M 25/0133; A61M 25/0662; A61M 2025/0166; A61M 2205/3368; A61M 2230/04; A61M 2230/50; A61M 25/0012
USPC ................ 600/372–374, 381, 393, 508–509; 606/22–42
See application file for complete search history.

(56) References Cited

U.S. PATENT DOCUMENTS

| | | | |
|---|---|---|---|
| 5,829,439 A | 11/1998 | Yokosawa et al. | |
| 6,010,511 A | 1/2000 | Murphy | |
| 6,083,170 A | 7/2000 | Ben-Haim | |
| 6,372,498 B2 | 4/2002 | Newman et al. | |
| 7,454,244 B2 | 11/2008 | Kassab et al. | |
| 7,818,053 B2 | 10/2010 | Kassab | |
| 7,963,929 B2 | 6/2011 | Kassab | |
| 8,078,274 B2 | 12/2011 | Kassab | |
| 8,082,032 B2 | 12/2011 | Kassab et al. | |
| 8,099,161 B2 | 1/2012 | Kassab | |
| 8,114,143 B2 | 2/2012 | Kassab et al. | |
| 9,259,161 B2 | 2/2016 | Suchecki et al. | |
| 2004/0097806 A1* | 5/2004 | Hunter ............... | A61B 1/00071 600/434 |
| 2004/0230131 A1 | 11/2004 | Kassab et al. | |
| 2005/0203434 A1 | 9/2005 | Kassab | |
| 2006/0074318 A1 | 4/2006 | Ahmed et al. | |
| 2006/0241482 A1 | 10/2006 | Karasawa | |
| 2007/0129717 A1* | 6/2007 | Brown ................ | A61B 5/015 606/41 |
| 2007/0264732 A1 | 11/2007 | Chen | |
| 2008/0033316 A1 | 2/2008 | Kassab et al. | |
| 2008/0161696 A1 | 7/2008 | Schmitt et al. | |
| 2008/0194996 A1 | 8/2008 | Kassab | |
| 2008/0234658 A1 | 9/2008 | Kassab et al. | |
| 2008/0294041 A1 | 11/2008 | Kassab | |
| 2009/0082698 A1 | 3/2009 | Kassab | |
| 2009/0118637 A1 | 5/2009 | Kassab et al. | |
| 2009/0171201 A1 | 7/2009 | Olson | |
| 2009/0182287 A1 | 7/2009 | Kassab | |
| 2009/0204029 A1 | 8/2009 | Kassab | |
| 2009/0204134 A1 | 8/2009 | Kassab | |
| 2009/0216133 A1 | 8/2009 | Kassab | |
| 2009/0299360 A1 | 12/2009 | Ormsby | |
| 2009/0319020 A1 | 12/2009 | Kassab | |
| 2010/0010355 A1 | 1/2010 | Kassab | |
| 2010/0010368 A1 | 1/2010 | Kassab | |
| 2010/0010488 A1 | 1/2010 | Kassab et al. | |
| 2010/0010503 A1 | 1/2010 | Kassab | |
| 2010/0030055 A1 | 2/2010 | Kassab | |
| 2010/0152607 A1 | 6/2010 | Kassab | |
| 2010/0168836 A1 | 7/2010 | Kassab | |
| 2010/0174271 A1 | 7/2010 | Kassab | |
| 2010/0222786 A1 | 9/2010 | Kassab | |
| 2010/0234698 A1 | 9/2010 | Manstrom et al. | |
| 2010/0249568 A1* | 9/2010 | Stehr .................. | A61B 5/053 600/374 |
| 2010/0249588 A1 | 9/2010 | Knight | |
| 2011/0034824 A1 | 2/2011 | Kassab | |
| 2011/0178383 A1 | 7/2011 | Kassab | |
| 2011/0178417 A1 | 7/2011 | Kassab | |
| 2011/0196255 A1 | 8/2011 | Kassab | |
| 2011/0196282 A1 | 8/2011 | Kassab | |
| 2011/0208109 A1 | 8/2011 | Kassab | |
| 2011/0245860 A1 | 10/2011 | Kassab | |
| 2011/0313341 A1 | 12/2011 | Kassab | |
| 2012/0053441 A1 | 3/2012 | Kassab | |
| 2012/0078342 A1* | 3/2012 | Vollkron ............. | A61B 5/0538 623/1.11 |
| 2012/0191181 A1 | 7/2012 | Kassab et al. | |
| 2012/0197113 A1 | 8/2012 | Courtney et al. | |
| 2012/0277725 A1 | 11/2012 | Kassab et al. | |
| 2012/0287750 A1 | 11/2012 | Deladi et al. | |
| 2012/0289951 A1 | 11/2012 | Kassab et al. | |
| 2012/0296368 A1 | 11/2012 | Kassab et al. | |
| 2013/0216114 A1 | 8/2013 | Courtney et al. | |
| 2014/0180083 A1 | 6/2014 | Hoseit | |

FOREIGN PATENT DOCUMENTS

| | | |
|---|---|---|
| JP | H04-329938 A | 11/1992 |
| JP | 2008136855 A | 6/2008 |
| WO | 9744089 A1 | 8/1998 |
| WO | 9835611 A1 | 8/1998 |
| WO | 9934724 A2 | 7/1999 |
| WO | 2006037082 A2 | 4/2006 |
| WO | 2008005388 A2 | 1/2008 |

OTHER PUBLICATIONS

European Patent Application No. 16163119.7, Extended European Search Report dated Jul. 28, 2016, 8 pages.

* cited by examiner

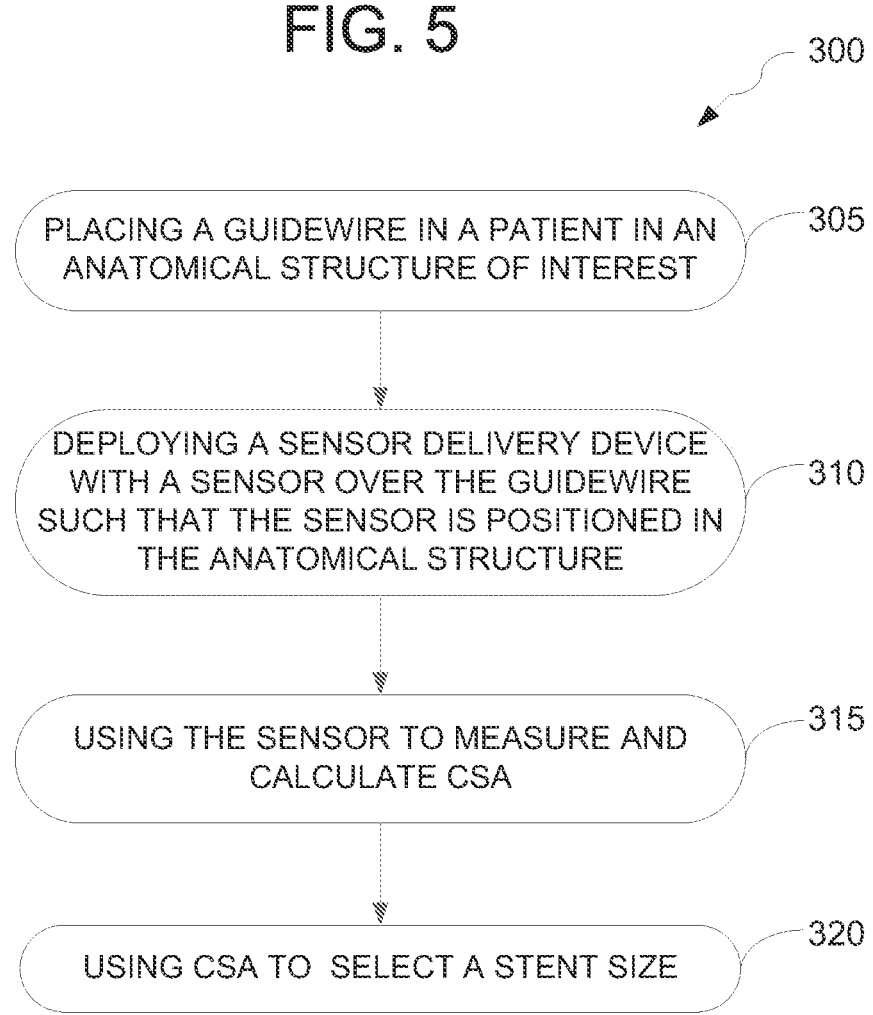

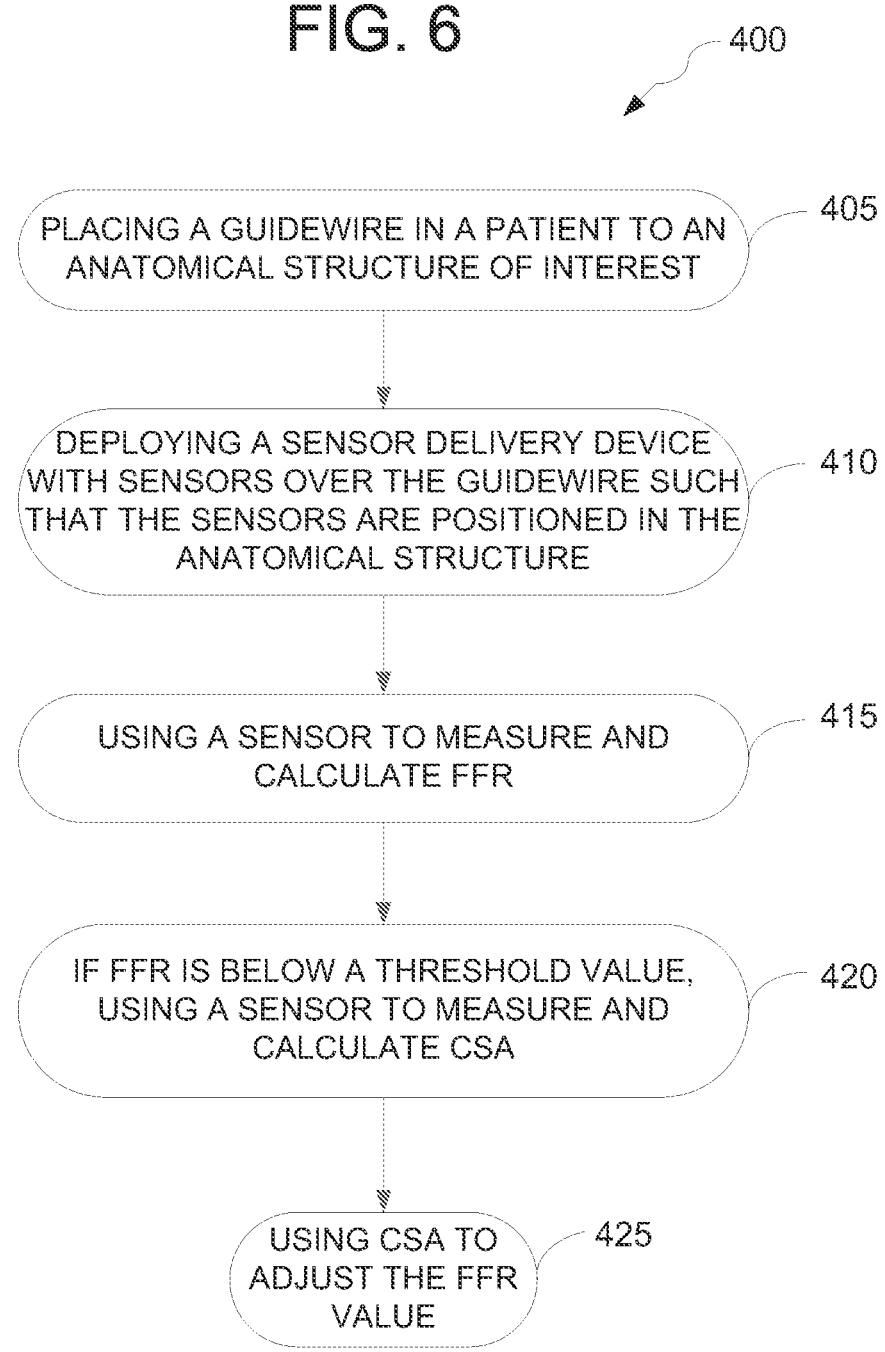

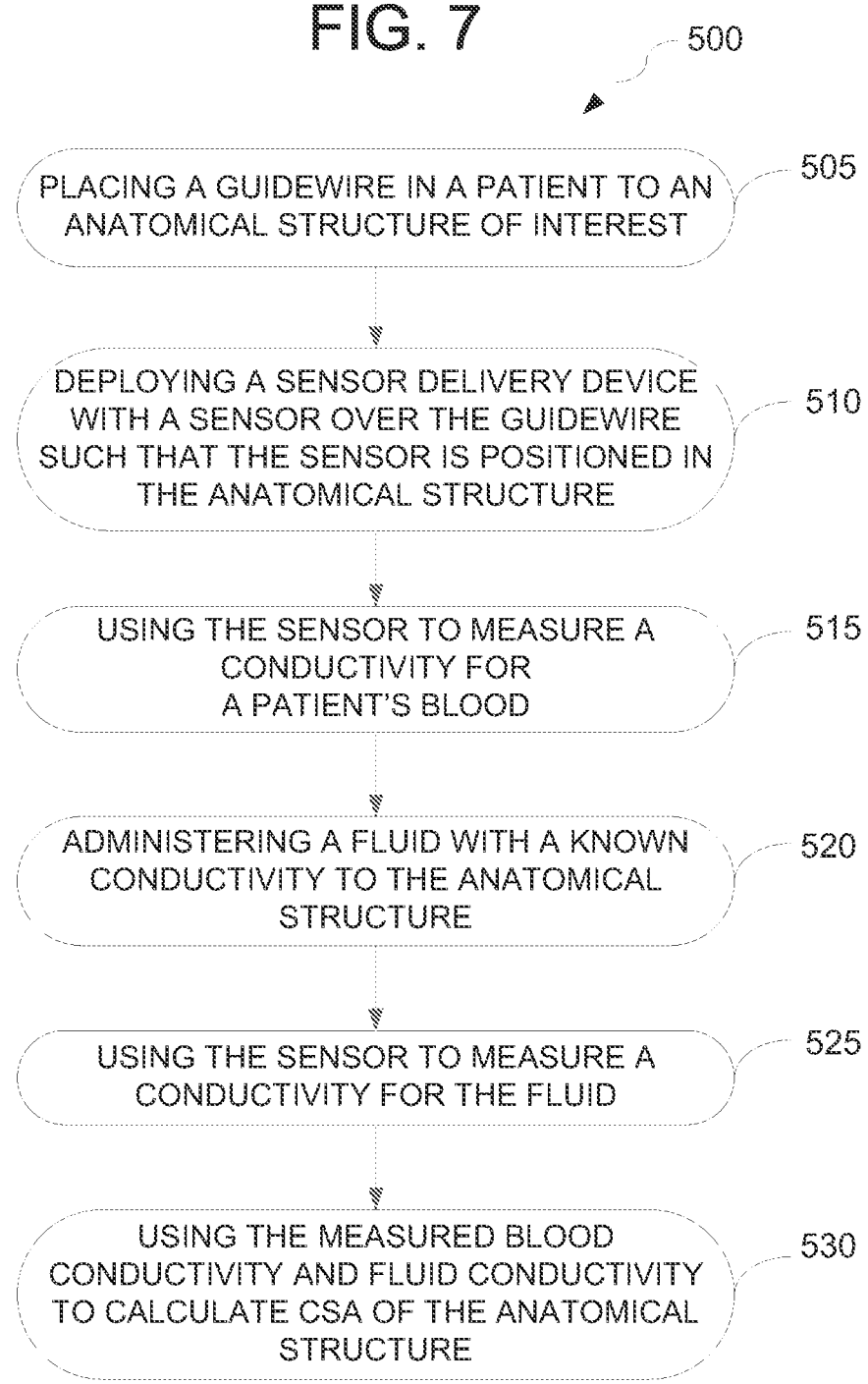

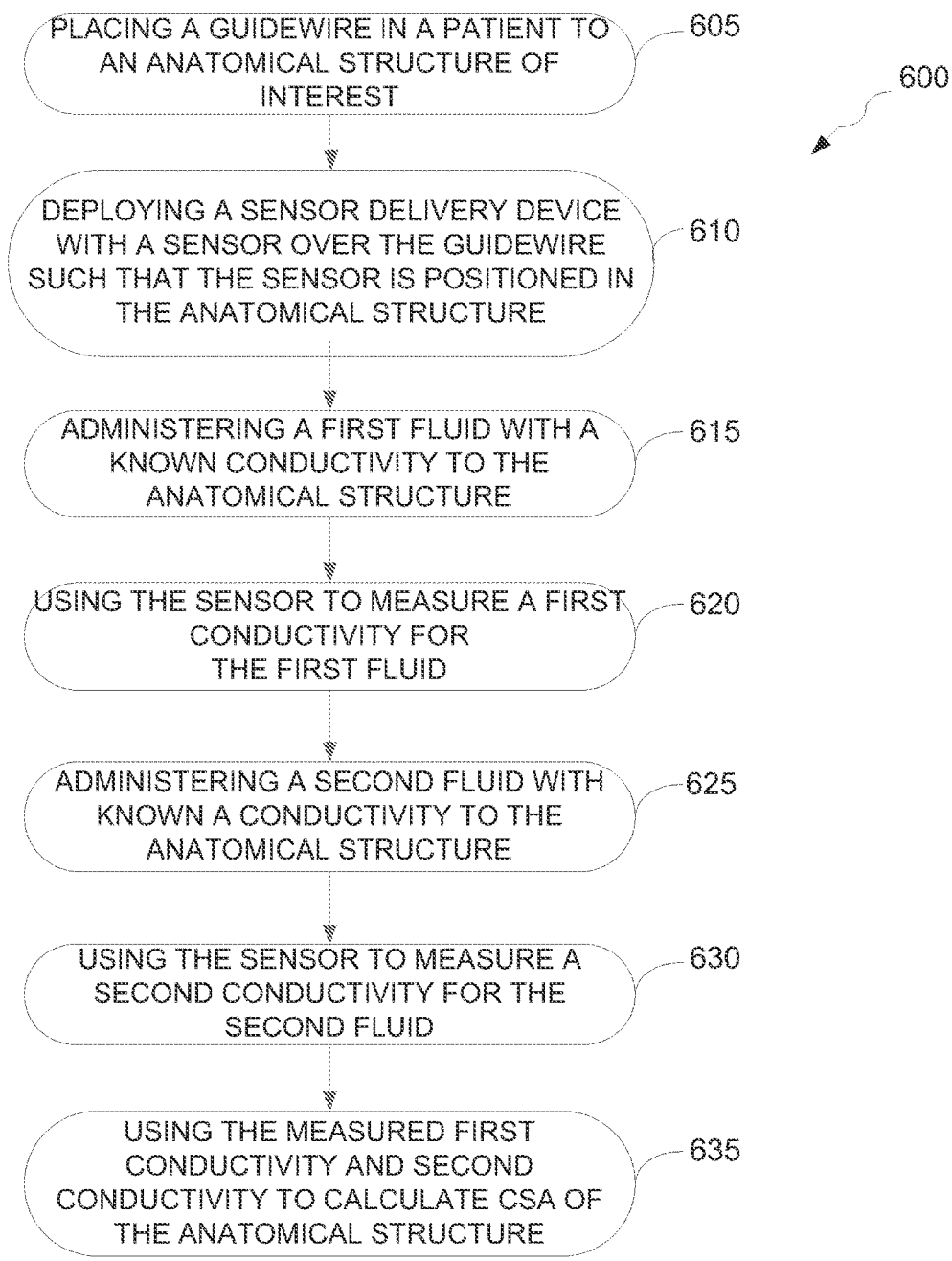

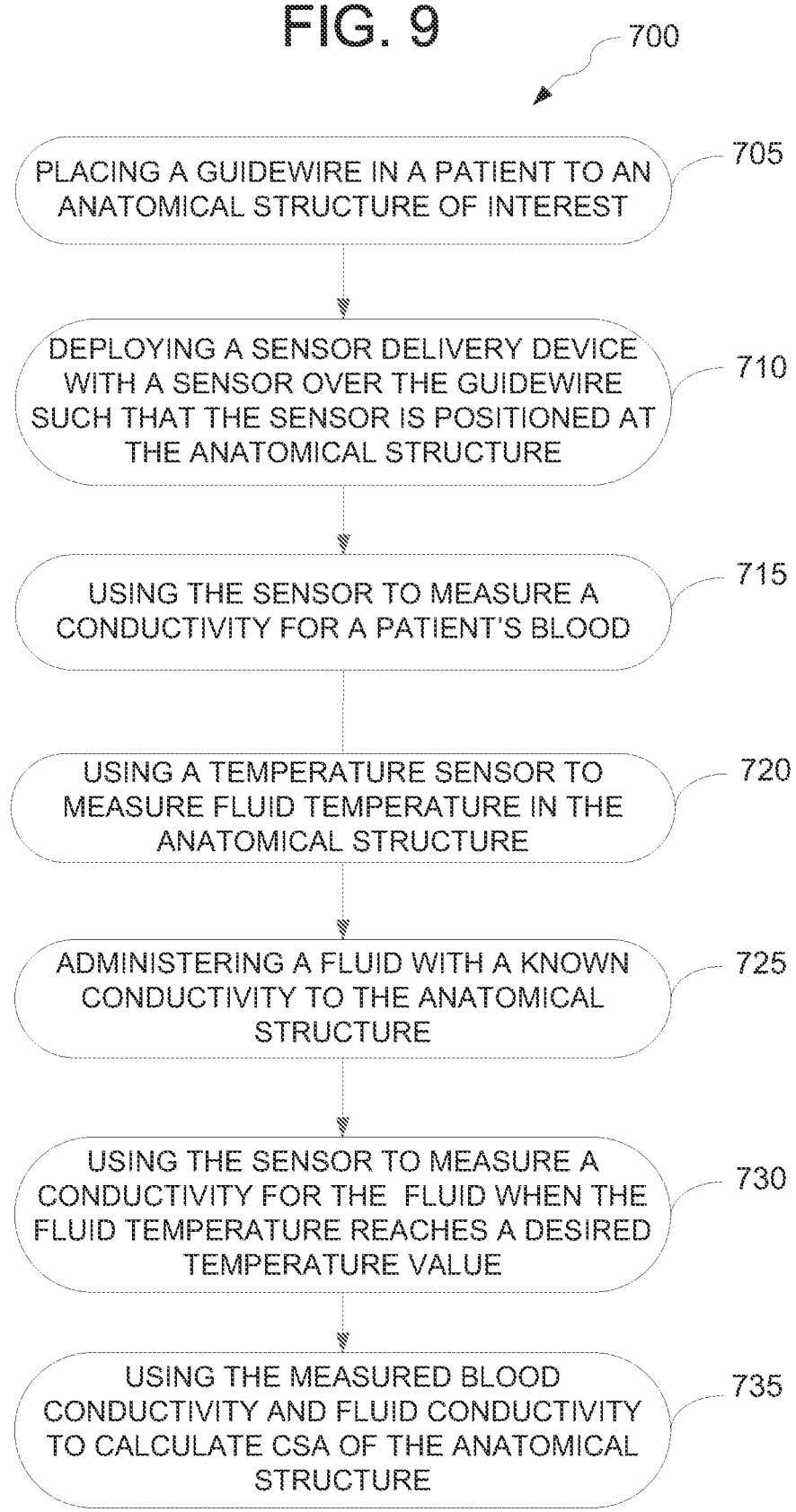

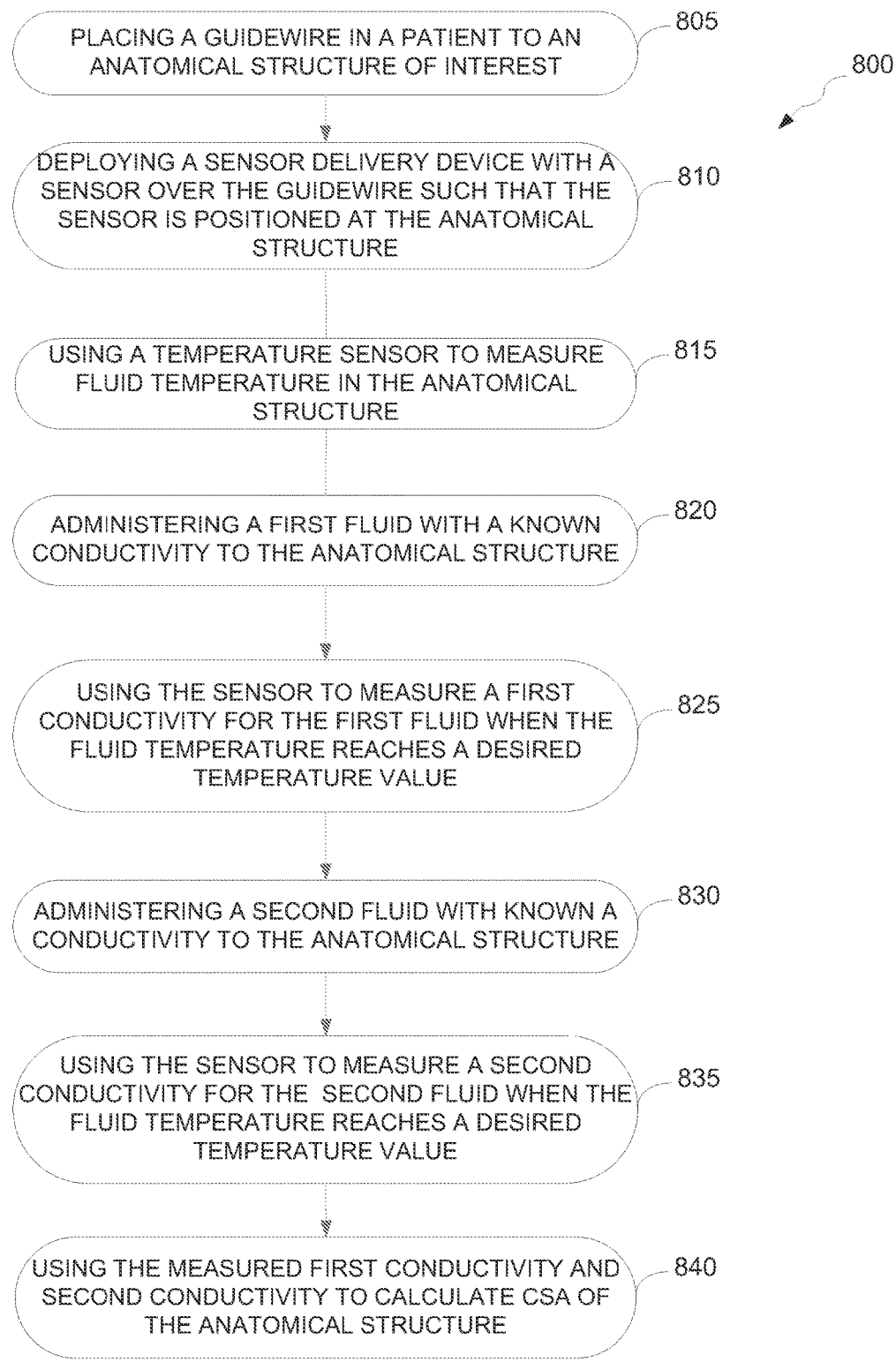

DEVICE AND METHODS FOR MEASURING AND TREATING AN ANATOMICAL STRUCTURE

FIELD

This application relates generally to the field of medical device technology and, more particularly, to devices and methods for positioning and utilizing physiological sensors in anatomical structures of patients, such as in blood vessels or across heart valves. This application also relates generally to methods for calculating cross-sectional areas of anatomical structures.

BACKGROUND

Patients sometimes experience stenosis in an anatomical structure. Stenosis occurs when an abnormal narrowing or stenotic lesion appears in the anatomical structure. Physicians generally evaluate the stenotic lesion before selecting a therapy to treat it. For example, in the case of blood vessels, if the stenotic lesion obstructs blood flow through the vessel to a large degree, physicians often elect to place a stent within the lesion site. On the other hand, if the stenotic lesion only minimally obstructs blood flow, physicians sometimes elect not to use a stent.

One technique for evaluating the degree to which a stenotic lesion obstructs flow through a blood vessel is called the Fractional Flow Reserve measurement (FFR). To calculate the FFR for a given stenotic lesion, two blood pressure readings are taken. One pressure reading is taken on the distal side of the lesion (e.g., downstream from the lesion) and the other pressure reading is taken on the proximal side of the lesion (e.g., upstream from the lesion, towards the aorta). The FFR is defined as the ratio of maximal blood flow in a stenotic lesion, taken distal to the lesion, to normal maximal flow, and is typically calculated based on a measured pressure gradient of the distal pressure to the proximal pressure. The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR.

The FFR measurement is considered a useful diagnostic tool. For example, clinical studies have shown that an FFR of less than about 0.8 or about 0.75 can be a useful criterion on which to base certain therapy decisions. A physician might decide, for example, to perform an interventional procedure (e.g., angioplasty or stent placement) when the FFR for a given stenotic lesion is below 0.8 or 0.75, and may decide to forego such treatment for lesions where the FFR is above 0.8 or 0.75. Thus, the FFR measurement provides a decision point for guiding treatment decisions.

Certain drawbacks are sometimes seen with the FFR method. First, the FFR method is designed merely to determine whether an interventional procedure such as a stent is needed or not needed. It does not provide any tools for enabling a physician to select a stent size that is ideal for the specific stenotic lesion at issue. Stents come in a variety of sizes, and physicians generally need to select an appropriate size and shape depending on the lesion characteristics. Physicians often need to use a separate procedure to determine what stent size to use. Commonly, physicians use an intravascular ultrasound method to determine a diameter of the vessel having the stenotic lesion. This method involves the advancement of a separate ultrasound catheter and the use of a separate ultrasound machine. This adds significant cost and time and more risk to the patient. Thus, it would also be desirable to provide a more simple system capable of both obtaining FFR measurements and selecting an appropriate stent size.

Another drawback seen with the FFR method is that the presence of a measuring device itself in the anatomical structure can affect the accuracy of the measurement. For example, as the measuring device crosses the stenotic lesion, the device itself introduces flow obstruction, in addition to that caused by the lesion itself. The measured distal pressure is sometimes lower than it would be without the additional flow obstruction, which may exaggerate the measured pressure gradient across the lesion. Thus, it would also be desirable to provide an improved system for obtaining more accurate FFR measurements.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIG. 5 is a flow diagram of a method of using the sensor delivery device to measure a cross-sectional area of an anatomical structure according to an embodiment of the invention;

FIG. 6 is a flow diagram of a method of using the sensor delivery device to measure and adjust a FFR value of an anatomical structure according to an embodiment of the invention;

FIG. 7 is a flow diagram of a method of using the sensor delivery device to measure blood conductivity and fluid conductivity to calculate a cross-sectional area of an anatomical structure according to an embodiment of the invention;

FIG. 8 is a flow diagram of a method of using the sensor delivery device to measure conductivity of a first fluid and a second fluid to calculate a cross-sectional area of an anatomical structure according to an embodiment of the invention;

FIG. 9 is a flow diagram of a method of using the sensor delivery device to measure blood conductivity and fluid conductivity to calculate a cross-sectional area of an anatomical structure according to another embodiment of the invention; and FIG. 10 is a flow diagram of a method of using the sensor delivery device to measure conductivity of a first fluid and a second fluid to calculate a cross-sectional area of an anatomical structure according to another embodiment of the invention.

SUMMARY

Figure 1:
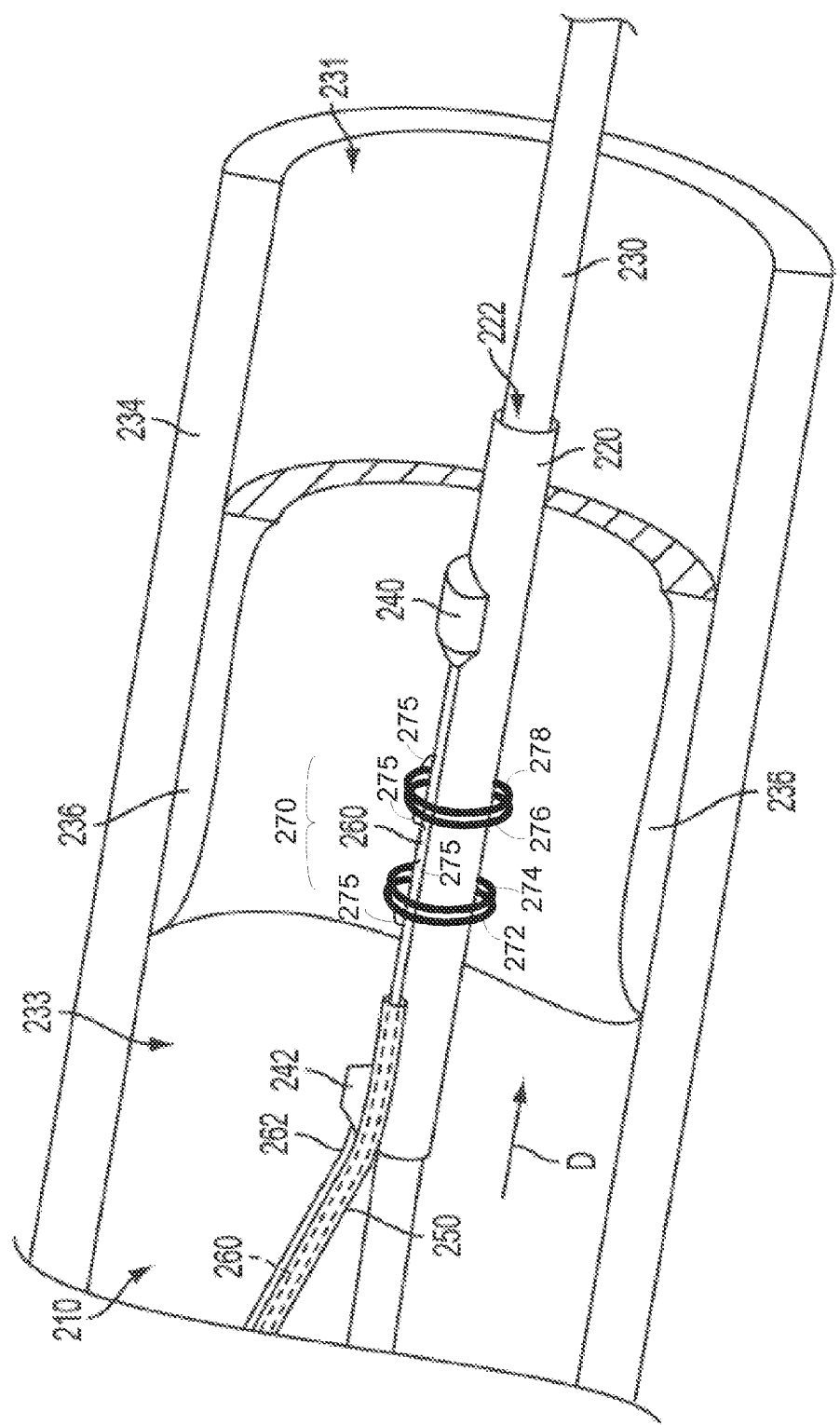
FIG. 1 is a perspective view of a sensor delivery device according to an embodiment of the invention.
Figure 1A:
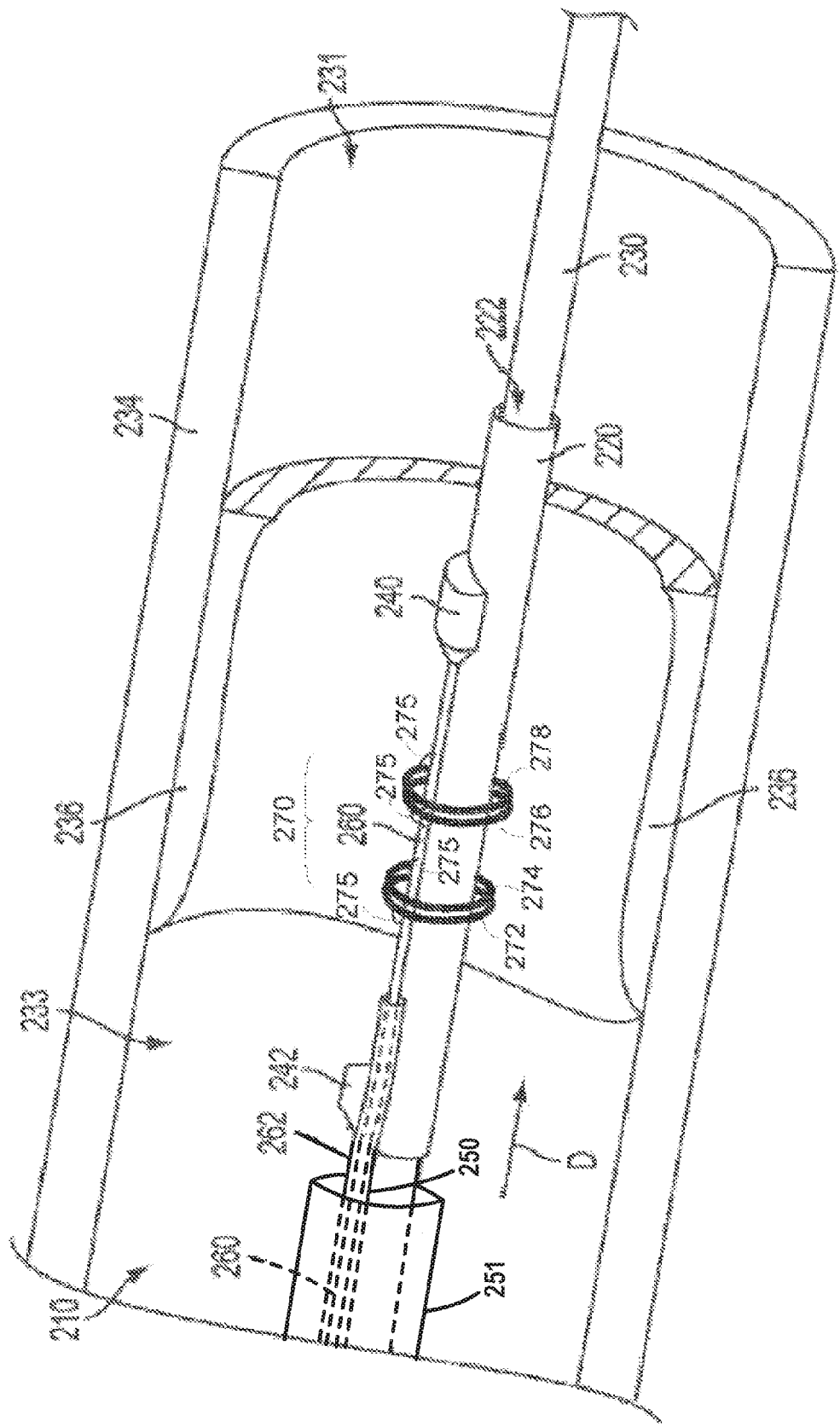
FIG. 1a is a perspective view of a sensor delivery device according to an embodiment of the invention.
Figure 1B:
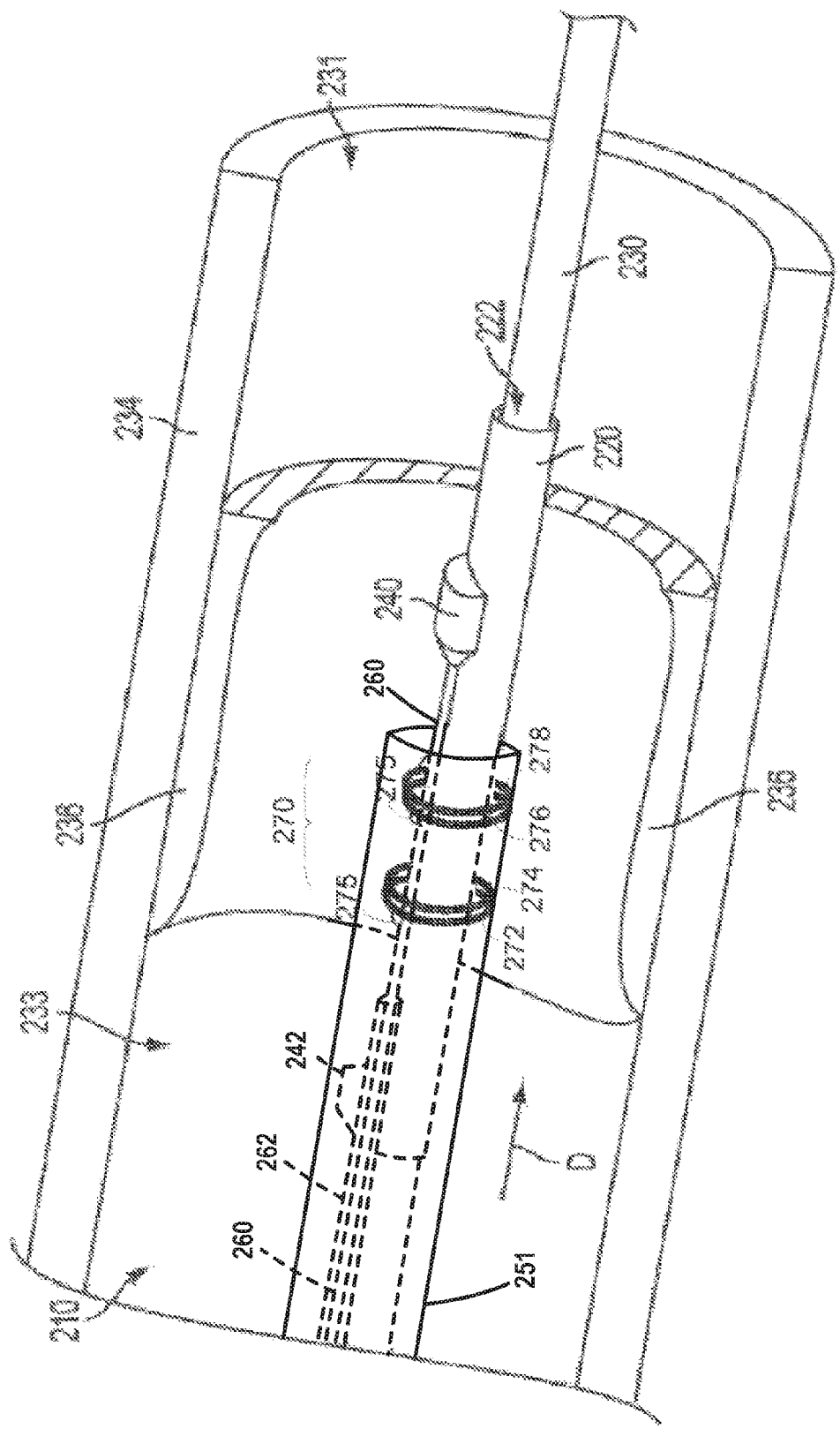
FIG. 1b is a perspective view of a sensor delivery device according to an embodiment of the invention.

Certain embodiments provide an intravascular sensor delivery device. The device can include a distal sleeve having a guidewire lumen for slidably receiving a medical guidewire, a first sensor coupled to the distal sleeve, wherein the first sensor is adapted to measure blood pressure and generate a signal representative of the blood pressure, a second sensor coupled to the distal sleeve, wherein the second sensor is adapted to measure cross-sectional area of a surrounding anatomical structure and generate a signal representative of the cross-sectional area, a proximal portion coupled to the distal sleeve, the proximal portion comprising a communication channel, wherein the communication channel communicates the signal from the first sensor and the signal from the second sensor to a location outside of the patient.

The second sensor of the intravascular sensor delivery device can be an electrode arrangement, for example an electrode arrangement that includes source electrodes and sense electrodes, wherein the source electrodes generate a current and the sense electrodes measure voltage resulting from the current. The signal representative of the cross-sectional area can be voltage measured by the sense electrodes. The source electrodes and the sense electrodes can also be ring-shaped electrodes that surround a periphery of the distal sleeve. The device can also include a movable sheath that is adapted to cover and uncover the electrode arrangement. The second sensor can be attached to an outer surface of the distal sleeve, perhaps at a location that is distal or proximal to the first sensor. In certain cases, the second sensor is coupled to both the distal sleeve and the proximal portion at a location that is proximal to the first sensor.

The intravascular sensor delivery device can also include third sensor. In such cases, the third sensor can be adapted to measure temperature and generate a signal representative of the temperature and wherein the communication channel communicates the signal from the first sensor, the signal from the second sensor, and the signal from the third sensor to a location outside of the patient. The first sensor and the third sensor can also be a single sensor, wherein the single sensor is adapted to both measure blood pressure and measure temperature.

Other embodiments provide an intravascular measuring system. The system can include a guidewire, an intravascular sensor delivery device, an injection device that is adapted to inject a fluid with a known conductivity to the anatomical structure, and a processor that is adapted to receive the first signal from the first sensor and the second signal from the second sensor. The injection device can be adapted to inject a first fluid (e.g., a NaCl solution having a first concentration, such as a 9% concentration) and a second fluid (e.g., a NaCl solution having a first concentration, such as a 4.5% concentration) into to the anatomical structure, wherein the first fluid has a first known conductivity and the second fluid has a second known conductivity, wherein the known conductivity of the first fluid is different than the known conductivity of the second fluid.

Further embodiments provide a method of determining cross-sectional area in an anatomical structure of a patient that includes steps of providing a sensor delivery device, wherein the sensor delivery device includes a distal sleeve having a guidewire lumen for slidably receiving a medical guidewire and a sensor coupled to the distal sleeve, wherein the sensor is adapted to measure fluid conductivity of a surrounding anatomical structure, (b) positioning the sensor delivery device within the anatomical structure, (c) administering a first fluid with a known conductivity to the anatomical structure (e.g., a NaCl solution having a first concentration, such as a 9% concentration), (d) using the sensor to measure a first conductivity for the first fluid, (e) administering a second fluid with a known conductivity to the anatomical structure (e.g., a NaCl solution having a first concentration, such as a 4.5% concentration), wherein the known conductivity of the first fluid is different than the known conductivity of the second fluid, (f) using the sensor to measure a second conductivity for the second fluid, and (g) using the first conductivity and the second conductivity to calculate a cross-sectional area of the anatomical structure.

Yet other embodiments provide a method of treating an anatomical structure in patient that includes steps of (a) providing a sensor delivery device, (b) positioning the sensor delivery device within the anatomical structure; (c) using the first sensor to obtain blood pressure measurements; (d) using the blood pressure measurements to calculate an FFR value; (e) electing to use a stent when the FFR value is lower than a threshold value, e.g., about 0.8, (f) using the second sensor to obtain one or more fluid conductivity measurements; (g) using the fluid conductivity measurements to calculate a cross-sectional area of the anatomical structure; and (h) using the cross-sectional area to select a stent size.

The step of using the cross-sectional area measurements to select a stent size can be a step of correlating a specific cross-sectional area measurement to a specific stent size. Also, the second sensor can be an electrode arrangement adapted to measure conductivity of fluid in the anatomical structure and the step of using the second sensor to obtain one or more cross-sectional area measurements can include steps of obtaining fluid conductivity measurements and calculating cross-sectional area measurements using the fluid conductivity measurements. The step of using the second sensor to obtain one or more cross-sectional area measurements can also include steps of (a) administering a first fluid (e.g., a NaCl solution having a first concentration, such as a 9% concentration)) with a known conductivity to the anatomical structure, (b) using the second sensor to measure a first conductivity for the first fluid, (c) administering a second fluid (e.g., a NaCl solution having a first concentration, such as a 4.5% concentration) with a known conductivity to the anatomical structure, wherein the conductivity of the first fluid is different than the conductivity of the second fluid, (d) using the second sensor to measure a second conductivity for the second fluid, and (e) using the first conductivity and the second conductivity to calculate a cross-sectional area of the anatomical structure.

The method can further include providing the sensor delivery device with a third sensor adapted to measure temperature of fluid in the anatomical structure, wherein the method includes steps of using the third sensor to measure fluid temperature and using the second sensor to obtain one or more cross-sectional area measurements after the fluid temperature reaches a desired temperature value.

Further embodiments provide a method of determining cross-sectional area in an anatomical structure of a patient that can include steps of (a) providing a sensor delivery device, wherein the sensor delivery device includes a distal sleeve having a guidewire lumen for slidably receiving a medical guidewire and a sensor coupled to the distal sleeve, wherein the sensor is adapted to measure fluid conductivity, (b) positioning the sensor delivery device within the anatomical structure, (c) using the sensor to measure a conductivity for the patient's blood, (d) administering fluid with a known conductivity to the anatomical structure, (e) using the sensor to measure a conductivity for the fluid, and (f) using the measured blood conductivity and the measured fluid conductivity to calculate a cross-sectional area of the anatomical structure.

DETAILED DESCRIPTION

For the purpose of promoting an understanding of the principles of the invention, reference will now be made to the embodiments illustrated in the drawing and specific language will be used to describe the same. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

In the foregoing detailed description, the invention has been described with reference to specific embodiments. However, it can be appreciated that various modifications and changes can be made without departing from the scope of the invention.

Figure 2:
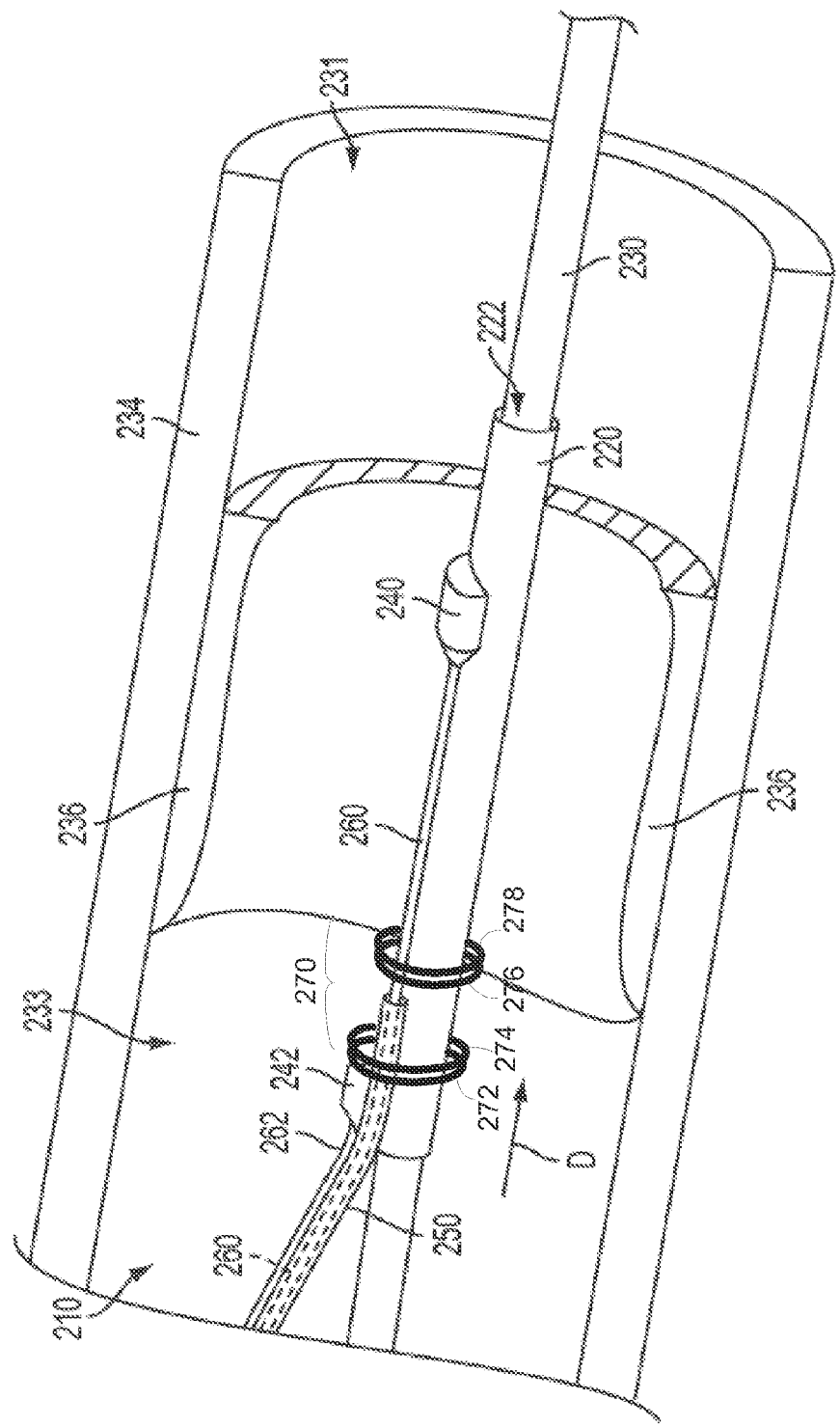
FIG. 2 is a perspective view of a sensor delivery device according to another embodiment of the invention.
Figure 3:
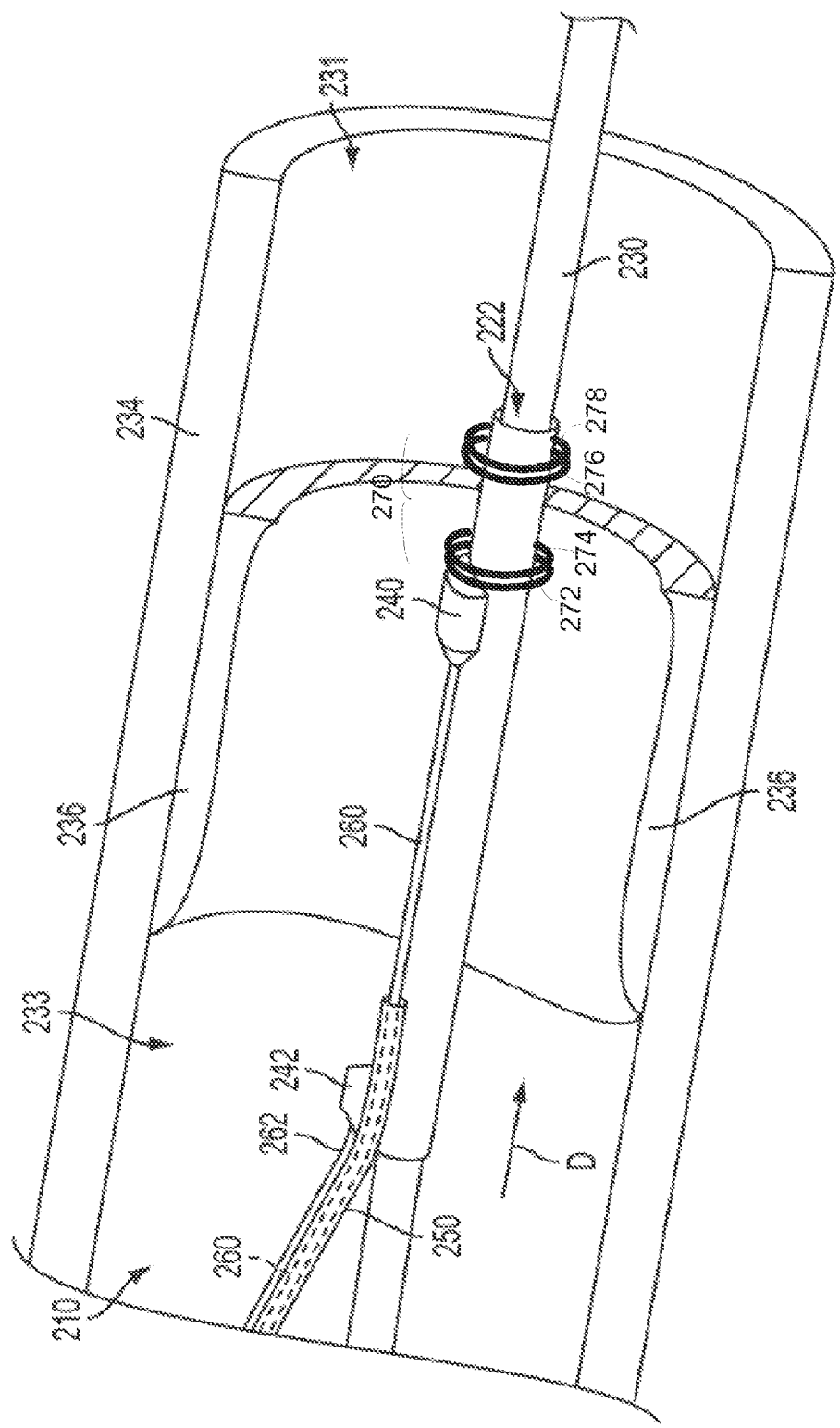
FIG. 3 is a perspective view of a sensor delivery device according to yet another embodiment of the invention.

FIGS. 1-3 show a sensor delivery device 210 being deployed in an anatomical structure. Here, the anatomical structure is a blood vessel of a patient (e.g., coronary artery 234) across a stenotic lesion 236. As used herein, the term "anatomical structure" refers to any body structure having a cross-sectional area or a hollow, tubular or luminal structure.

The sensor delivery device 210 includes a distal sleeve 220 having a guidewire lumen 222 for slidably receiving a medical guidewire 230. A first sensor 240 and a second sensor 270 are each coupled to the distal sleeve 220. The first sensor 240 is capable of measuring blood pressure in the anatomical structure and generating a signal representative of the blood pressure. The second sensor 270 is capable of measuring cross-sectional area of the anatomical structure and generating a signal representative of the cross-sectional area. In some cases, the delivery device also includes a third sensor that is adapted to measure temperature of fluid in the anatomical structure and generate a signal representative of the temperature. In some cases, the first sensor and third sensor are combined into a single sensor that measures both blood pressure and temperature.

While the terms "first sensor," "second sensor," and "third sensor" are used herein, each of these terms are not limited to single or separate sensors. Skilled artisans would understand that any number of sensors can be used for each the "first sensor," "second sensor," and/or the "third sensor." Likewise, the "first sensor," "second sensor," and/or the "third sensor" can be combined into a single sensor. Moreover, any of the sensors described herein can be provided on any of the embodiments described in U.S. Patent Publication No. 2010/0234698 (application Ser. No. 12/557,685), the entire contents of which are incorporated herein by reference.

The first sensor 240 is adapted to measure blood pressure and generate a signal representative of the blood pressure. In certain embodiments, the first sensor 240 is a fiber optic pressure sensor adapted to measure blood pressure. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In other embodiments, first sensor 240 can be a piezo-resistive pressure sensor (e.g., a MEMS piezo-resistive pressure sensor). In yet other embodiments, first sensor 240 can be a capacitive pressure sensor (e.g., a MEMS capacitive pressure sensor). A pressure sensing range from about −50 mm Hg to about +300 mm Hg (relative to atmospheric pressure) is desired for making most physiological measurements with the first sensor 240, for example.

The second sensor 270 can include any sensor type that is capable of measuring a cross-sectional area of a surrounding anatomical structure. In some cases, the sensor 270 measure conductivity of fluid in an anatomical structure. The fluid conductivity measurements can then be used to calculate a cross-sectional area measurement. In FIGS. 1-3, the second sensor 270 is an electrode arrangement that includes source electrodes 272, 274 and sense electrodes 276, 278. The source electrodes 272, 274 deliver a current and the sense electrodes 276, 278 measure voltage resulting from the current. The voltage measurement from the sense electrodes 276, 278 can be used to calculate the fluid conductivity and thus the cross-sectional area of the surrounding anatomical structure. Examples of suitable algorithms and methods for calculating a cross-sectional area measurement using voltage and/or fluid conductivity measurements can be found in U.S. Pat. No. 7,454,244 (application Ser. No. 10/782,149), the entire contents of which are incorporated herein by reference.

The sensor delivery device 10 also includes a proximal portion 250, which is coupled to the distal sleeve 220. The proximal portion 250 includes a communication channel 260 and the sensors are communicably connected to the communication channel 260. The communication channel communicates signals from the sensors to a location outside of the patient (e.g., to a processor, display, computer, monitor, or to another medical device). The communication channel 260 can be any suitable channel that transmits signals generated by the sensors to a location outside of the patient. Exemplary communication channels include fiber optic, electrically conductive, wireless, infrared, acoustic, and/or ultrasound mediums. The communication channel 260 can be disposed along an outer surface of proximal portion 250, or can be formed within the proximal portion 250, as shown in FIGS. 1-3. For example, the communication channel 260 can be a communication lumen that extends longitudinally through proximal portion 250 in some embodiments.

The first sensor 240, the second sensor 270 and the third sensor are each coupled to a distal sleeve 220. The sensors can be provided at any suitable location along the distal sleeve 220. In some cases, the sensors can be provided on an outer surface of the distal sleeve 220.

FIGS. 1-3 each show an electrode arrangement 270 that is coupled to the distal sleeve 220 at different locations. In FIG. 1, each of the electrodes 272, 274, 276, 278 are coupled to the distal sleeve 220 at a position that is proximal to the first sensor 240. In FIG. 2, the source electrodes 272, 274 are coupled to both the distal sleeve 220 and the proximal portion 250 whereas the sense electrodes 276, 278 coupled only to the distal sleeve. Specifically, the sense electrodes are coupled to the distal sleeve 220 at a position that is distal to the proximal portion 250 and proximal to the first sensor

240. In FIG. 3, each of the electrodes 272, 274, 276, 278 are coupled to the distal sleeve 220 at a position that is distal to the first sensor 240.

In FIGS. 1-3, the electrodes 272, 274, 276, 278 each have a ring shape so that they surround a circumference or periphery of the distal sleeve (and proximal portion in some embodiments). Of course, the electrodes 272, 274, 276, 278 can instead be point electrodes or have other suitable configurations. The electrodes 272, 274, 276, 278 can also be made of any suitable conductive material such as platinum iridium or a carbon-coasted surface. Additionally, the electrodes 272, 274, 276, 278 can be provided in communication with the communication channel 260 using any desired method. For example, in FIG. 1, one or more wires 275 connect the electrodes 272, 274, 276, 278 to the communication channel 60.

In certain embodiments, the sensor delivery device further includes a movable sheath 251, wherein the movable sheath 251 is adapted to cover and uncover the sensor 270 or the electrode arrangement 270. Such a movable sheath is valuable in cases where it is desired to trap the patient's blood between the sheath and the electrodes, as will be further discussed below.

The proximal portion 250 is also adapted to assist an operator in positioning the distal sleeve 220 and the sensors within the anatomical structure of the patient. This is typically accomplished by an operator first inserting a "standard" medical guidewire 230 into a patient's vasculature and advancing it to an anatomical structure of interest. The sensor delivery device 210 is then deployed by "threading" the distal sleeve 220 onto the guidewire 230 such that the lumen 222 slides over the guidewire 230, and advancing the distal sleeve 220 (and the associated sensors) by moving (e.g., pushing and/or pulling) the proximal portion 250 until sensors are in the desired location. Thus, the distal sleeve 220, and hence, the sensors, can be positioned within an anatomical structure of a patient by causing the distal sleeve 220 to slide over the medical guidewire 230 to the desired position.

The proximal portion 250 can also be formed of a material of sufficient stiffness in order to assist an operator in positioning the distal sleeve 220 and the sensors within an anatomical structure of the patient. Suitable materials for the proximal portion 250 can be materials such as stainless steel, nitinol, nylon, and plastic, for example, or composites of multiple materials. Depending on the application, the proximal portion 250 can be made stiffer and more rigid than the distal sleeve 220 in order to provide a reasonable amount of control to push, pull and otherwise maneuver the device to the location of interest within the patient.

The device 210 and the guidewire 230 are typically manipulated inside a guiding catheter (not shown), which has been placed in the anatomical structure of interest. In certain embodiments of the invention, the guidewire lumen 222 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, in certain preferred embodiments of the invention, the guidewire lumen 222 may be sized appropriately to slide over a particular standard size medical guidewire. A device according to preferred embodiments of the invention may therefore be made available in a range of sizes corresponding to standard medical guidewire sizes.

In certain embodiments of the invention, the distal sleeve 220 of the device can be substantially concentric with the guidewire 230. The coupling of the proximal portion 250 to the distal sleeve 220 allows the guidewire 320 to separate from the rest of device 210 (e.g., in what is sometimes referred to as a "monorail" catheter configuration); this would typically occur inside a guiding catheter. The guidewire 230 and device 210 would both exit the patient at the proximal end of a guiding catheter as separate devices. Having the device 210 and guidewire 230 separate allows the physician to independently control device 210 and guidewire 230, as necessary. It may also allow a physician to use a shorter guidewire for catheter exchange. For example, a monorail-type configuration may allow for the use of a guidewire that is approximately 170 to 200 cm long, whereas an "over-the-wire" configuration might require the use of a much longer (e.g., up to 300 cm or more) guidewire. Having the device 210 and guidewire 230 separate (except at the distal sleeve 220) may also result in less friction than if the device 210 and guidewire 230 had to be moved together as a unit. In some embodiments, a hydrophilic coating may be applied to various portions of the device to further reduce the amount of friction encountered, for example, when advancing or retracting device 210.

The distal sleeve 220 can be substantially tubular, as shown, or can have any shape that allows distal sleeve 220 to slide over a medical guidewire 230 in an anatomical structure of interest. The distal sleeve 220 can be formed of a flexible material in some embodiments to facilitate positioning and placement of the distal sleeve 220 (and sensors) over a guidewire 230 through narrow vascular structures such as coronary arteries. In certain embodiments, the distal sleeve 220 comprises a flexible polyimide tube or flexible microcoil tube sized for placement in vascular structures, such as in coronary arteries or peripheral arteries. In some embodiments, flexibility may be achieved and/or enhanced by applying a series of cuts along the surface of the distal sleeve 220. The length of distal sleeve 220 can also vary. In embodiments to be used deep within coronary arteries, for example, distal sleeve 220 can be up to about 15 inches long. The distal sleeve 220 can also include a thin covering to provide additional structural support and/or improve handling characteristics of the device. Such a covering can comprise, for example, polyester (PET) shrink tubing that substantially covers the distal sleeve.

One advantage of the sensor delivery device 210 is that it does not require repositioning of the guidewire in order to make multiple sensor readings. Once the guidewire has been positioned across a stenotic lesion, for example, the sensor delivery device 210 can be positioned (e.g., advanced and/or retracted) over the guidewire and the sensors can therefore be advanced and retracted across lesions to make pressure, temperature and cross-sectional area readings, for example, without moving the guidewire. A physician may also save time by not having to reposition the guidewire across the lesion or lesions to make such measurements.

Figure 4:
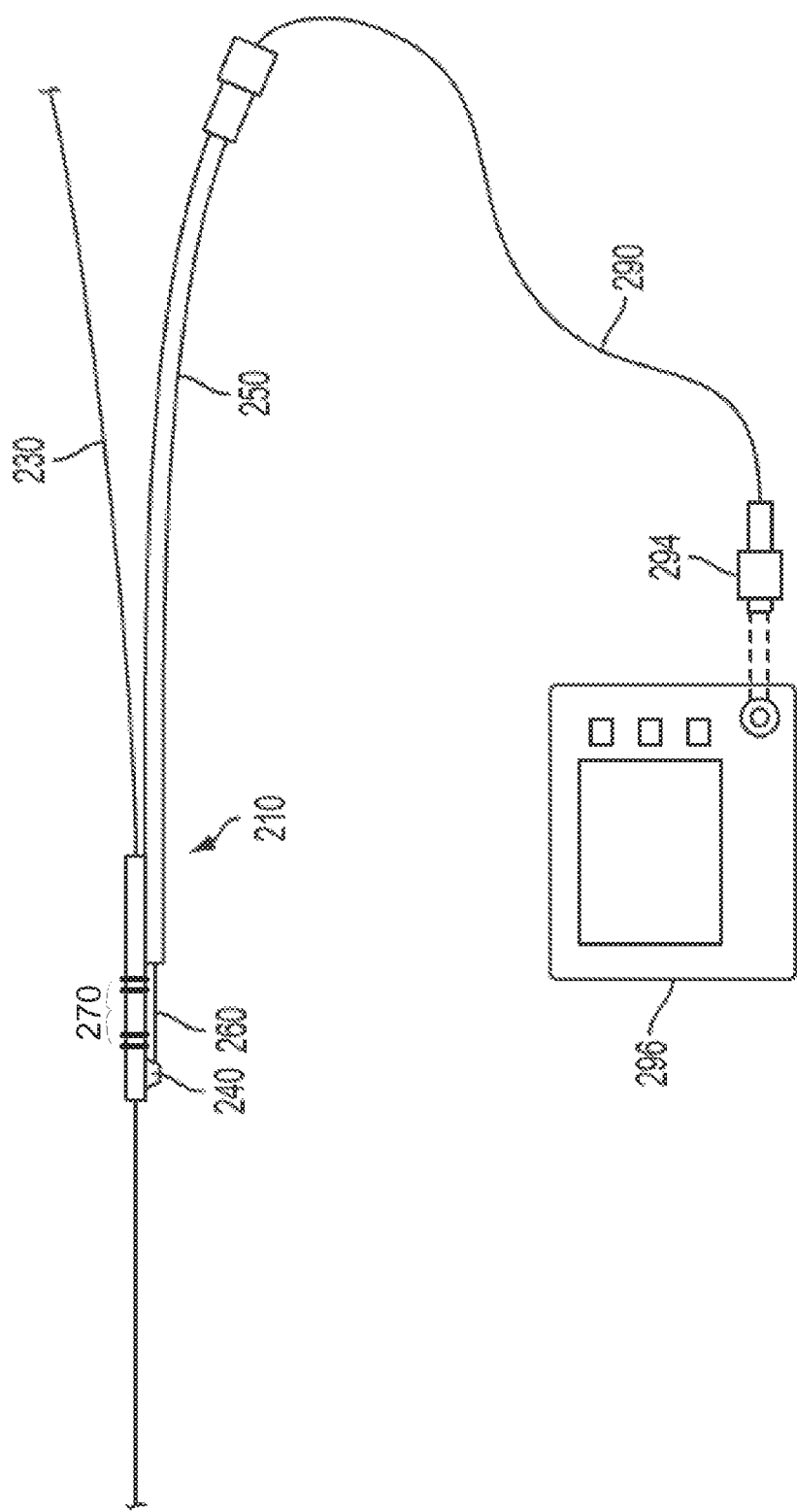
FIG. 4 is a perspective view of a sensor delivery device having a furncation tube according to an embodiment of the invention.

The sensor delivery device 210 can also interact with other devices and/or display equipment. In some embodiments, as shown in FIG. 4, the sensor delivery device 210 interacts with a processor 296. The sensor delivery device 210 and processor 296 can interact using any known connection mechanism in the art. In certain cases, a furcation tube 290 and a connector 294 can be used to send signals from the sensors 240, 270 to the processor 296. The processor 296 can be, for example, a standalone display monitor to show signal waveforms and/or numerical values of the signals from sensors 240, 270. The processor 296 could include data recording capabilities in some embodiments.

The processor 296 is adapted to receive signals from each of the sensors and to use those signals to make calculations. Typically, the processor 296 uses one or more algorithms to make calculations. For example, in cases where the sensor 270 is an electrode arrangement, the electrode arrangement obtains a voltage measurement representative of the conductivity of the surrounding fluid and then sends that measurement to the processor 296. The processor 296 then uses the measured voltage to calculate fluid conductivity and thus cross-sectional area of the anatomical structure.

In other embodiments, the sensor delivery device 210 also interacts with a medical fluid injection device, such as a powered fluid injector used to inject contrast media and/or saline during certain medical procedures (e.g., angiography, computed tomography, MRI, ultrasound, etc.). Exemplary powered injection systems that can be used with the sensor delivery device 210 are described in U.S. Patent Publication No. 2010/0234698 (application Ser. No. 12/557,685), the entire contents of which are incorporated herein by reference. In some embodiments, the injection device is adapted to inject a first fluid and a second fluid into the anatomical structure. Typically, the first fluid has a first known conductivity and the second fluid has a second known conductivity, wherein the known conductivity of the first fluid is different than the known conductivity of the second fluid. In certain embodiments, the first fluid can be a NaCl solution having a first concentration and the second fluid can be a NaCl solution having a second concentration, wherein the first concentration is higher than the second concentration. As an example, the first fluid can be a NaCl solution having a 9% concentration and the second fluid can be a NaCl solution having a 4.5% concentration.

FIGS. 5-10 are flow diagrams that illustrate certain methods of using the sensor delivery device. Each of these methods will now be described. FIG. 5 is a flow diagram that illustrates a method 300 of using the sensor delivery device to measure a cross-sectional area of an anatomical structure. Step 305 comprises a guidewire into the patient and into an anatomical structure of interest. Step 310 comprises deploying a sensor delivery device 210 including one or more sensors over the guidewire and positions the device (and thus the sensors) in the anatomical structure. Step 315 comprises using one of the sensors to measure and calculate cross-sectional area of the anatomical structure. Finally, step 320 comprises using the cross-sectional area calculation to select a stent size for the anatomical structure. In certain cases, the stent size is selected by correlating a specific cross-sectional area measurement to a specific stent size.

FIG. 6 is a flow diagram of a method 400 of using the sensor delivery device to measure and adjust a FFR value of an anatomical structure. Step 405 comprises placing a guidewire into the patient and into an anatomical structure of interest. Step 410 comprises deploying a sensor delivery device 210 including one or more sensors over the guidewire and positions the device (and thus the sensors) in the anatomical structure. Step 415 comprises using one of the sensors to measure and calculate an initial FFR value. Exemplary methods and algorithms for calculating an FFR value are described in U.S. Patent Publication No. 2010/0234698 (application Ser. No. 12/557,685), the entire contents of which are incorporated herein by reference. Step 410 comprises using one of the sensors to measure and calculate cross-sectional area. Step 425 comprises using the initial FFR value and cross-sectional area to calculate a corrected FFR value.

FIG. 7 is a flow diagram of a method 500 of using the sensor delivery device to measure blood conductivity and fluid conductivity to calculate a cross-sectional area of an anatomical structure. Step 505 comprises placing a guidewire into the patient and into an anatomical structure of interest. Step 510 comprises deploying a sensor delivery device 210 including one or more sensors over the guidewire and positions the device (and thus the sensors) in the anatomical structure. Step 515 comprises using one of the sensors to measure a conductivity of the patient's blood. Step 520 comprises administering a fluid with a known conductivity to the anatomical structure. Step 525 comprises using one of the sensors to measure a conductivity of the fluid. Finally, step 530 comprises using the measured blood conductivity and fluid conductivity to calculate a cross-sectional area of the anatomical structure. Exemplary methods of using measured conductivities to calculate a cross-sectional area of an anatomical structure can be found in U.S. Pat. No. 7,454,244 (application Ser. No. 10/782,149), the entire contents of which are incorporated herein by reference.

FIG. 8 is a flow diagram of a method 600 of using the sensor delivery device to measure conductivity of a first fluid and a second fluid to calculate a cross-sectional area of an anatomical structure. Step 605 comprises placing a guidewire into the patient and into an anatomical structure of interest. Step 610 comprises deploying a sensor delivery device 210 including one or more sensors over the guidewire and positioning the device (and thus the sensors) in the anatomical structure. Step 615 comprises administering a first fluid with a known conductivity to the anatomical structure. Step 620 comprises using one of the sensors to measure a first conductivity for the first fluid. Step 625 comprises administering a second fluid with a known conductivity to the anatomical structure. Step 630 comprises using the sensor to measure a second conductivity for the second fluid. Finally, step 635 comprises using the measured first conductivity and second conductivity to calculate cross-sectional area of the anatomical structure.

FIG. 9 is a flow diagram of a method 700 of using the sensor delivery device to measure blood conductivity and fluid conductivity to calculate a cross-sectional area of an anatomical structure. Step 705 comprises placing a guidewire into the patient and into an anatomical structure of interest. Step 710 comprises deploying a sensor delivery device 210 including one or more sensors over the guidewire and positioning the device (and thus the sensors) in the anatomical structure. Step 715 comprises using one of the sensors to measure conductivity for a patient's blood. Step 720 comprises using a temperature sensor to measure fluid temperature in the anatomical structure. Step 725 comprises administering a fluid with a known conductivity to the anatomical structure. Step 730 comprises using one of the sensors to measure conductivity of the fluid when the fluid temperature reaches a desired temperature value. Step 735 comprises using the measured blood conductivity and fluid conductivity to calculate cross-sectional area of the anatomical structure.

FIG. 10 is a flow diagram of a method 800 of using the sensor delivery device to measure conductivity of a first fluid and a second fluid to calculate a cross-sectional area of an anatomical structure. Step 805 comprises placing a guidewire into the patient and into an anatomical structure of interest. Step 810 comprises deploying a sensor delivery device 210 including one or more sensors over the guidewire and positioning the device (and thus the sensors) in the anatomical structure. Step 815 comprises using a temperature sensor to measure fluid temperature in the anatomical structure. Step 820 comprises administering a first fluid with a known conductivity to the anatomical structure. Step 825 comprises using one of the sensors to measure a first conductivity for the first fluid when the fluid temperature reaches a desired temperature value. Step 830 comprises administering a second fluid with a known conductivity to the anatomical structure. Step 835 comprises using one of the sensors to measure a second conductivity for the second fluid when the fluid temperature reaches a desired temperature value. Finally, step 840 comprises using the measured first conductivity and second conductivity to calculate cross-sectional area of the anatomical structure.

Certain specific embodiments of the methods illustrated in FIGS. 5-10 will now be described. In certain embodiments, a method is provided that enables a physician to first determine an FFR value of an anatomical structure and then to calculate cross-sectional area of the anatomical structure in order to select an appropriate stent size. Such a method includes providing a sensor delivery device, wherein the sensor delivery device includes a first sensor that is adapted to measure blood pressure and a second sensor that is adapted to measure cross-sectional area of the anatomical structure, positioning the sensor delivery device within the anatomical structure, using the first sensor to obtain one or more blood pressure measurements, using the blood pressure measurements to calculate an FFR value, electing to use a stent when the FFR value is lower than a threshold value, using the second sensor to obtain one or more cross-sectional area measurements, and using the cross-sectional area measurements to select a stent size. The FFR threshold value can be about 0.8, for example. In many cases, the step of using the cross-sectional area measurements to select a stent size comprises correlating a specific cross-sectional area measurement to a specific stent size.

In other embodiments, a method is provided that includes enables a physician to obtain an initial FFR value of an anatomical structure and then to calculate fluid conductivity measurements of fluid of the anatomical structure in order to correct or adjust the initial FFR value. Such a method includes providing a sensor delivery device, wherein the sensor delivery device includes a first sensor is adapted to measure blood pressure and a second sensor adapted to measure conductivity of fluid in the anatomical structure, positioning the sensor delivery device within the anatomical structure, using the first sensor to obtain one or more blood pressure measurements, using the blood pressure measurements to calculate an initial FFR value, using the second sensor to obtain one or more cross-sectional area measurements, using the cross-sectional area measurements to calculate a corrected FFR value. The corrected FFR value closer to what the FFR value would have been if the sensor delivery device was not present (or if just a guidewire was present) in the anatomical structure. In certain cases, the corrected FFR value is calculated using an algorithm that combines the initial FFR value with the cross-sectional area measurements. The algorithm could also account for cross-sectional area measurements taken proximal and/or distal to the stenotic lesion and the volumetric flow rate or blood velocity. The method can further include electing to use a stent when the corrected FFR value is beneath a threshold value, for example a value of about 0.8. In this case, the method can even further include using the cross-sectional area to select a stent size.

In certain embodiments, the second sensor is used to measure fluid conductivity, which can then be used to calculate a cross-sectional area of the anatomical structure. Typically, the second sensor measures fluid conductivities for two different fluids and uses those conductivity measurements to calculate cross-sectional area. In some cases, two fluids other than the patient's blood are used. In such cases, the method includes administering a first fluid with a known conductivity to the anatomical structure, using the second sensor to measure a first conductivity for the first fluid, administering a second fluid with a known conductivity to the anatomical structure, wherein the conductivity of the first fluid is different than the conductivity of the second fluid, using the second sensor to measure a second conductivity for the second fluid, and using the first conductivity and the second conductivity to calculate a cross-sectional area of the anatomical structure. In certain embodiments, the first fluid is a NaCl solution having a first concentration, for example a 9% concentration, and the second solution is a NaCl solution having a second concentration, for example a 4.5% concentration, wherein the first concentration is higher than the second concentration.

In other cases, the patient's blood is used as one of the fluids if its conductivity is known. In such cases, the method includes using the second sensor to measure conductivity for the patient's blood, administering fluid with a known conductivity to the anatomical structure, using the second sensor to measure conductivity for the fluid, and using the measured blood conductivity and the measured fluid conductivity to calculate a cross-sectional area of the anatomical structure. Using the patient's blood as one of the fluids is advantageous because it eliminates having to perform two fluid administrations, which provides time savings and convenience. In certain cases, the sensor delivery device can include a movable sheath that is movable by a user to cover and uncover the second sensor. For example, when the second sensor is an electrode arrangement, the sheath covers and uncovers the electrodes. When moved to cover the electrodes, the sheath traps a small amount of the patient's blood between the electrodes and the conductivity of the blood can be directly measured. This allows for the amount of current used by the electrodes for such a blood conductivity measurement to be less than the amount of current needed to measure a fluid in the surrounding anatomical structure.

In each of these methods, the second sensor can be an electrode arrangement that is adapted to measure fluid conductivity. In such cases, the method includes using the electrodes to obtain fluid conductivity measurements and calculating cross-sectional area measurements using the fluid conductivity measurements. In certain preferred cases, the electrode arrangement includes source electrodes and sense electrodes, wherein the source electrodes generate a current, for example a constant current, and the sense electrodes measure voltage resulting from the current. As such, in some cases, the method comprises obtaining voltage measurements and calculating fluid conductivity (and thus calculating cross-sectional area measurements) using the voltage measurements.

In embodiments where the second sensor is an electrode arrangement, the electrodes can also measure blood flow velocity. For example, the electrode arrangement can be configured to measure resistance between the source electrodes (for example between a first and a second source electrode) and the resistance between sense electrodes (for example between a first and a second sense electrode). When a fluid having conductivity different than the patient's blood travels past the electrodes, the time difference in when the measured change in resistance occurs on each set of electrodes can be used to measure the blood flow velocity at the anatomical structure. In other words, the blood flow velocity can be calculated by dividing the time difference by the distance between these sets of electrodes. The blood flow velocity measurement and the cross-sectional area measurement can also both be used to calculate a volumetric blood flow.

In certain cases, the above methods can also include providing a third sensor, wherein the third sensor is a temperature sensor that measures temperature of fluid in the anatomical structure. The third sensor and the first sensor can be a single sensor in some embodiments, wherein the single sensor is adapted to measure both blood pressure and fluid temperature. Such a temperature sensor is useful because it provides the ability to create a timing signal that the physician and/or processor could use to determine when the fluid (which has a lower temperature than blood) is present in the anatomical structure. For example, in cases where the second sensor measures conductivity of patient's blood and an outside fluid, the method comprises using the second sensor to measure a conductivity for the patient's blood, administering fluid with a known conductivity to the anatomical structure, using the third sensor to measure fluid temperature, using the second sensor to measure a conductivity for the fluid after the fluid temperature reaches a desired temperature value, and using the measured blood conductivity and the measured fluid conductivity to calculate a cross-sectional area of the anatomical structure.

Likewise, in cases where the second sensor measures conductivities of two fluids other than a patient's blood, the method comprises administering a first fluid with a known conductivity to the anatomical structure, using the third sensor to measure fluid temperature, using the second sensor to measure a conductivity for the first fluid after the fluid temperature reaches a desired temperature value, administering a second fluid with a known conductivity to the anatomical structure, wherein the conductivity of the first fluid is different than the conductivity of the second fluid, using the second sensor to measure a conductivity for the second fluid after the fluid temperature reaches a desired temperature value, and using the first conductivity and the second conductivity to calculate a cross-sectional area of the anatomical structure.

Further, in cases where a third sensor or temperature sensor is used, both the fluid conductivities and the temperature can be measured and recorded in real time. Such a real time or continuous recording arrangement provides several advantages. First, when a fluid is injected, a user and/or processor can select a fluid conductivity measurement that corresponds to the lowest temperature measurement (or select the lowest fluid conductivity measurement obtained). This ensures that the measurement selected is actually the measurement of the injected fluid. Also, a real time measuring system allows for a user to continuously monitor the fluid conductivity while the sensor delivery device is moved through the body. Once the sensor delivery device is placed near or within the anatomical structure of interest, the user can manipulate the device until the lowest fluid conductivity measurement is located. At this point, the user then fixes the device at that location in order to perform the above-described methods. This allows for a user to fix the device at a location that likely has a minimum lumen diameter and is thus a location that is most affected by the stenosis.

EXAMPLE

The following steps illustrate one exemplary method of the invention.

1) A clinician identifies a stenotic lesion via angiogram.
2) The clinician determines that the lesion is "intermediate," that is, it is not clear whether or not intervention (e.g., stenting) would be beneficial or harmful to the patient.
3) The clinician inserts the sensor delivery device including sensors into place and equalizes to aortic pressure.
4) The clinician administers adenosine.
5) The clinician calculates a FFR value using a sensor on the sensor delivery device.
6) If the FFR value is below a certain threshold value, the clinician decides to insert a stent.
7) With the sensory delivery device still in place, the clinician measures cross-sectional area (CSA) as follows:
   a. A first conductance value (C1) is measured (with blood in lumen).
   b. 0.9% saline is administered (injected) while measuring and/or monitoring conductance. The minimum reading is recorded as C2.
   c. 0.45% saline is administered (injected) while measuring and/or monitoring conductance. The minimum reading is recorded as C3.
   d. C3 and C2 are utilized along with known fluid conductivities to calculate CSA.
   e. Alternatively, C1 is used along with a separate measurement of blood conductivity (e.g., C2), to calculate CSA, and the C3 measurement could be dropped.
8) The clinician uses the CSA measurement to select a stent size.
9) The clinician inserts the appropriately sized stent into the stenotic lesion.
10) The sensor delivery device can also include a special marker band with a pattern recognizable to a computer algorithm. Based on locating the marker band, a computer could automatically place visual information (such as the FFR reading and/or the vessel sizing information) on the angiogram itself.

What is claimed is:

1. An intravascular measuring system comprising:
an intravascular sensor delivery device that includes:
   a distal sleeve having a guidewire lumen for slidably receiving a medical guidewire;
   a first sensor coupled to the distal sleeve;
   a second sensor coupled to the distal sleeve, wherein the second sensor comprises an electrode arrangement including source electrodes and sense electrodes;
   a sheath adapted to trap an amount of blood between the source electrodes and the sense electrodes by being movable to cover the electrode arrangement; and
   a proximal portion coupled to the distal sleeve, the proximal portion comprising a communication channel; and
a processor in communication with the communication channel of the intravascular sensor delivery device, the processor being adapted to:
   receive a first signal from the first sensor, the first signal being representative of a blood pressure measured by the first sensor;

provide a source signal to the second sensor while the electrode arrangement is covered by the sheath, the source signal causing the source electrodes to generate a current;

receive a second signal from the second sensor while the electrode arrangement is covered by the sheath, the second signal being representative of a voltage sensed by the sense electrodes resulting from the current generated by the source electrodes;

calculate a blood conductivity based on the second signal.

2. The system of claim 1 wherein the processor is further adapted to calculate a cross-sectional area based on the calculated blood conductivity.

3. The system of claim 1 wherein the electrode arrangement includes two source electrodes and two sense electrodes.

4. The system of claim 1 wherein the source electrodes and the sense electrodes are ring-shaped electrodes that surround a periphery of the distal sleeve.

5. The system of claim 1 wherein the second sensor is attached to an outer surface of the distal sleeve.

6. The system of claim 1 wherein the second sensor is coupled to the distal sleeve at a location that is distal to the first sensor.

7. The system of claim 1 wherein the second sensor is coupled to the distal sleeve at a location that is proximal to the first sensor.

8. The system of claim 1 wherein the second sensor is coupled to both the distal sleeve and the proximal portion at a location that is proximal to the first sensor.

9. The system of claim 1 wherein the intravascular sensor delivery device further comprises a third sensor, wherein the processor is further adapted to receive a third signal from the third sensor, the third signal being representative of a temperature measured by the third sensor.

10. The system of claim 9 wherein the first sensor and the third sensor are a single sensor, wherein the single sensor is adapted to both measure blood pressure and measure temperature.

11. The system of claim 2 wherein the processor is adapted to use one or more algorithms to calculate the cross-sectional area.

12. An intravascular measuring system comprising:
a guidewire;
an intravascular sensor delivery device that has a lumen that slidably receives the guidewire, the sensor delivery device including a first sensor, a second sensor, and a movable sheath;
wherein the first sensor is adapted to measure a blood pressure and generate a first signal representative of the blood pressure; and
wherein the second sensor comprises an electrode arrangement including source electrodes that generate a current and sense electrodes that measure voltage resulting from the current and generate a second signal representative of a conductivity of the surrounding fluid, wherein the movable sheath is adapted to trap an amount of blood between the source electrodes and the sense electrodes by being movable to cover the electrode arrangement; and
a processor that is adapted to:
provide a source signal to the source electrodes while the electrode arrangement is covered by the movable sheath;
receive the first signal from the first sensor and the second signal from the second sensor while the electrode arrangement is covered by the movable sheath; and
calculate a cross-sectional area of the surrounding anatomical structure based on the first signal and the second signal.

13. The intravascular measuring system of claim 12 wherein the sensor delivery device comprises:
a distal sleeve having the lumen for slidably receiving the guidewire, wherein both the first sensor and the second sensor are coupled to the distal sleeve; and
a proximal portion coupled to the distal sleeve, the proximal portion comprising a communication channel, wherein the communication channel communicates the signal from the first sensor and the signal from the second sensor to the processor.

14. The intravascular measuring system of claim 12 wherein the processor is adapted to receive signals from each of the sensors and to use those signals to make calculations.

15. The intravascular measuring system of claim 14 wherein the processor uses one or more algorithms to make calculations.

16. The intravascular measuring system of claim 14 wherein the processor calculates the cross-sectional area of the surrounding anatomical structure by using measured voltage to calculate fluid conductivity.

17. The intravascular measuring system of claim 12 wherein the processor can be, for example, a standalone display monitor to show signal waveforms and/or numerical values of the signals from sensors.

18. The intravascular measuring system of claim 12 wherein the processor can include data recording capabilities.

19. The device of claim 12 wherein the electrode arrangement includes two source electrodes and two sense electrodes.

20. The device of claim 12 wherein the source electrodes and the sense electrodes are ring-shaped electrodes that surround a periphery of the distal sleeve.

21. The device of claim 12 wherein the second sensor is attached to an outer surface of the distal sleeve.

22. The device of claim 12 wherein the second sensor is coupled to the distal sleeve at a location that is distal to the first sensor.

23. The device of claim 12 wherein the second sensor is coupled to the distal sleeve at a location that is proximal to the first sensor.

24. The device of claim 12 wherein the second sensor is coupled to both the distal sleeve and the proximal portion at a location that is proximal to the first sensor.

25. The intravascular measuring system of claim 12 wherein the sensor delivery device further comprises a third sensor, wherein the third sensor is adapted to measure temperature and generate a third signal representative of the temperature and wherein the processor is adapted to receive the first signal from the first sensor, the second signal from the second sensor, and the third signal from the third sensor.

26. The device of claim 25 wherein the first sensor and the third sensor are a single sensor, wherein the single sensor is adapted to both measure blood pressure and measure temperature.

* * * * *